(12) United States Patent
Skender et al.

(10) Patent No.: US 10,814,041 B2
(45) Date of Patent: Oct. 27, 2020

(54) GRAFT MATERIAL AND METHOD OF USE THEREOF

(71) Applicant: COOK MEDICAL TECHNOLOGIES LLC, Bloomington, IN (US)

(72) Inventors: Davorin Kevin Skender, Bloomington, IN (US); Ralf Spindler, Solsberry, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 89 days.

(21) Appl. No.: 16/100,516

(22) Filed: Aug. 10, 2018

(65) Prior Publication Data

US 2019/0060528 A1 Feb. 28, 2019

Related U.S. Application Data

(60) Provisional application No. 62/551,351, filed on Aug. 29, 2017.

(51) Int. Cl.
| | |
|---|---|
| *A61F 2/07* | (2013.01) |
| *A61L 31/02* | (2006.01) |
| *D04B 1/22* | (2006.01) |
| *D03D 1/00* | (2006.01) |
| *A61L 31/04* | (2006.01) |
| *A61L 31/06* | (2006.01) |

(52) U.S. Cl.
CPC .......... *A61L 31/028* (2013.01); *A61F 2/07* (2013.01); *A61L 31/048* (2013.01); *A61L 31/06* (2013.01); *D03D 1/00* (2013.01); *D04B 1/22* (2013.01); *A61F 2002/072* (2013.01); *A61L 2400/12* (2013.01); *D03D 2700/0174* (2013.01); *D10B 2509/06* (2013.01)

(58) Field of Classification Search
CPC ........................................................ A61F 2/07
See application file for complete search history.

(56) References Cited

U.S. PATENT DOCUMENTS

| | | | |
|---|---|---|---|
| 7,162,308 B2 | 1/2007 | O'Brien et al. | |
| 7,758,572 B2 | 7/2010 | Weber et al. | |
| 8,048,028 B2 | 11/2011 | Horn et al. | |
| 8,187,221 B2 | 5/2012 | Bates | |
| 8,585,753 B2 | 11/2013 | Scanlon et al. | |
| 2006/0052865 A1 | 3/2006 | Banas | |
| 2006/0173397 A1 | 8/2006 | Tu et al. | |
| 2006/0184112 A1* | 8/2006 | Horn | A61L 29/126 604/103.08 |
| 2007/0191766 A1 | 8/2007 | McMorrow | |
| 2009/0171440 A1 | 7/2009 | Carlson et al. | |

(Continued)

OTHER PUBLICATIONS

Extended European Search Report for 18275134.7 dated Jan. 24, 2019, 8 pgs.

(Continued)

*Primary Examiner* — Matthew W Schall
(74) *Attorney, Agent, or Firm* — Brinks Gilson & Lione (57) ABSTRACT

The present disclosure relates to woven and knitted fabrics including boron nitride nanotubes and to methods of manufacturing and using such materials. In one embodiment, these materials are incorporated into implantable medical devices such as stent graft devices and the like.

19 Claims, 4 Drawing Sheets (56) References Cited

U.S. PATENT DOCUMENTS

2012/0016297 A1 1/2012 D'Aquanni et al.
2012/0114734 A1 5/2012 Desai et al.

OTHER PUBLICATIONS

Bhagwat, Surbhi S., "Dynamic Analysis of Boron Nitride Nanotube Reinforced Nano Composite Coronary Stents," International Journal for Technological Research in Engineering, vol. 2, Issue 7, Mar. 2015, pp. 810-815.

Karagkiozaki, Varvara et al., Abstract of "Novel Nanostructured Biomaterials: Implications for Coronary Stent Thrombosis," International Journal of Nanomedicine, vol. 7, 2012, pp. 6063-6076.

Tiano, Amanda L., et al. "Boron Nitride Nanotube: Synthesis and Applications," Proc. SPIE 9060, Nanosensors, Biosensors, and Info-Tech Sensors and Systems, 2014, 19 pages.

* cited by examiner

GRAFT MATERIAL AND METHOD OF USE THEREOF

RELATED APPLICATIONS

This application claims the benefit of priority of U.S. Provisional application Ser. No. 62/551,351 filed on Aug. 29, 2017, which application is incorporated by reference herein in its entirety.

TECHNICAL

The present disclosure relates to woven and knitted fabrics including boron nitride nanotubes and to methods of manufacturing and using such materials. In one embodiment, these materials are incorporated into implantable medical devices such as stent graft devices and the like.

BACKGROUND

Implantable medical devices, particularly endoluminally deployable medical devices, are known for a variety of medical applications including the treatment of aneurysms. Aneurysms occur in blood vessels at sites where, due to age, disease or genetic predisposition, the strength or resilience of the vessel wall is insufficient to prevent ballooning or stretching of the wall as blood flows therethrough. If the aneurysm is left untreated, the blood vessel wall may expand to a point at which rupture occurs, often leading to death.

To prevent rupturing of an aneurysm, such as an abdominal aortic aneurysm, a stent graft may be introduced into a blood vessel percutaneously and deployed to span the aneurysmal sac. The outer surface of each end of the stent graft is preferably sealed against the interior wall of the blood vessel at a site where the interior wall has not suffered a loss of strength or resilience. Blood flowing through the vessel is channeled through the hollow interior of the stent graft to reduce, if not eliminate, the stress on the vessel wall at the location of the aneurysmal sac. Therefore, the risk of rupture of the blood vessel wall at the aneurysmal location is significantly reduced or eliminated, and blood can pass through the vessel without interruption.

Stent grafts include a graft fabric secured to a stent. The graft is typically inserted into or pulled over the stent and sewn to its structural components. Alternatively, the stent may be formed on the graft such that the individual wires of the stent are threaded through specially provided projecting fabric loops on the surface of the graft. The stent provides rigidity and structure to hold the graft open in a tubular configuration as well as the outward radial force needed to create a seal between the graft and the vessel wall. The graft provides the tubular channel for blood flow past the aneurysm and prevents blood from pressurizing the aneurysmal sac.

However, current stent-graft cover material is known to sometimes exhibit a lack of stability. This may have life-threatening consequences when devices incorporating such material rupture after being implanted.

SUMMARY

The present invention provides an improved medical device and a method of preparing and using such a device. According to an aspect of the present invention, there is provided a fabric comprising a knitted or woven textile material and a plurality of boron nitride nanotubes, wherein the boron nitride nanotubes are present in a matrix between strands of the knitted or woven textile material or within the strands of the knitted or woven textile material.

The textile material may include, for example, a polyester, polyethylene terephthalate, a fluorinated polymer, polytetrafluoroethylene (PTFE), expanded PTFE, a polyurethane, polyethylene, polypropylene, polyaramid, polyacrylonitrile, nylon or cellulose or a combination of such materials. In a preferred embodiment, the textile material includes polyethylene terephthalate.

In one embodiment, the boron nitride nanotubes are present in the strands of the knitted or woven textile material. In another embodiment, the strands include a plurality of filaments of the textile material, where the filaments are either twisted or untwisted, and where the BNNTs are continuously integrated along the filaments. In yet another embodiment, the filaments are twisted and the BNNTs are discontinuously integrated along the filaments. In other embodiments, the strands include a plurality of twisted fibers of the textile material and the BNNTs are wrapped around a least a portion, or the entire length, of an outside surface of the strand.

Another aspect of the invention provides a medical device including a stent having a luminal surface and an abluminal surface and a woven or knitted textile graft including BNNTs as disclosed herein. The stent may be at least partly formed from, for example, a metal, a metal alloy or a polymeric material. In various embodiments, the textile material includes a polyester, polyethylene terephthalate, a fluorinated polymer, polytetrafluoroethylene (PTFE), expanded PTFE, a polyurethane, polyethylene, polypropylene, polyaramid, polyacrylonitrile, nylon, cellulose or a combination of at least two of these materials.

BRIEF DESCRIPTION OF THE DRAWINGS

Embodiments of the present invention are described below, by way of example only, with reference to the accompanying drawings, in which:

FIGS. 6(A-B) are illustrations showing functionalizing of a thread within a knitted textile arrangement with BNNTs. In FIG. 6(A), a single thread (dark thread) is functionalized with BNNTs. FIG. 6(B) shows an arrangement. in which a vertical row of "loops" is functionalized with BNNTs.

DESCRIPTION OF THE PREFERRED EMBODIMENTS

It is to be understood that the drawings are schematic only and not to scale. Often only the principal components relevant to the teachings herein are shown in the drawings, for the sake of clarity.

The term "implantable medical device" refers to a medical device that is either permanently or temporarily inserted into a patient's body for treatment of a medical condition.

The term "strand" refers to a monofilament (e.g., a thread) or to a plurality of filaments (e.g., a yarn), with or without twist, which is suitable for weaving, knitting, or otherwise interlacing to form a fabric.

As used herein, the term "warp" refers to the strand of a woven fabric what is held in tension on a frame or loom to create the fabric. The term "weft" refers to the strand that is drawn through, inserted over-and-under, the warp strand. Warp is the lengthwise or longitudinal strand in a roll, while weft is the transverse strand.

The term "woven" may refer to a fabric formed in a plain weave characterized by a regular, one-to-one interlacing of warp and weft strands. That is, each strand aligned in a warp direction moves alternatively over and under adjacent strands aligned in the welt direction. This basic plain weave produces the maximum number of binding points (i.e., intersections of a single strand in the warp direction with strands in the welt direction), and is thus a firm, durable weave. However, the woven fabric may have any known weave, such as a basket weave, a rep or rib weave, a twill weave (e.g., straight twill, reverse twill, herringbone twill), a satin weave, or a double weave (e.g., double-width, tubular double weave, reversed double weave).

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a drug means an amount of the drug which imparts a therapeutic effect to the human or veterinary patient.

Implantable Devices Incorporating Boron Nitride Nanotubes

On aspect of the present invention provides implantable medical devices incorporating boron nitride nanotubes (BNNTs). BNNTs are a polymorph of boron nitride. They are structurally similar to the carbon nanotube, which are cylinders with sub-micrometer diameters and micrometer length, except that carbon atoms are alternately substituted by nitrogen and boron atoms. However, certain properties of BNNTs are very different and offer advantages over carbon nanotubes in the construction of implantable devices.

Whereas carbon nanotubes can be metallic or semiconducting depending on the rolling direction and radius, BNNTs act as an electrical insulator independent of tube chirality and morphology. This causes implantable devices including BNNTs to be more MRI compatible than similar devices incorporating carbon nanotubes. Because they are insulators, BNNTs do not act as antennas and therefore do not heat up then subject to the MRI radio frequency.

BNNTs are more thermally stable than carbon nanotubes. They exhibit oxidation resistance up to 800° C. in air, whereas carbon nanotubes are only stable up to 300-400° C. This thermal stability allows BNNTs to be used at the high process temperatures and pressures which are often used during the processing of devices such as stent grafts. Furthermore, chemical changes, such as oxidation, which may affect the biological compatibly of the device, can be prevented. BNNTs also maintain their strength at temperatures up to about 900° C., whereas carbon nanotubes start losing strength at 400° C.

BNNTs may also be prepared with longer tube lengths than carbon nanotubes. This improves the ability to withstand tensile forces during crimping and expansion of devices such as stent grafts. Large size networks may also be manufactured with BNNTs. This allows for the prevention of creep and rupture of stent cover material incorporating BNNTs and for the formation of a thin reinforcement layer.

Established techniques of carbon nanotube production, such as arc-discharge, laser ablation and chemical vapor deposition, may be used for mass-production of BNNTs at a tens of grams scale. These nanotubes can also be produced by ball milling of amorphous boron, mixed with a catalyst (iron powder), under $NH_3$ atmosphere. Subsequent annealing at ~1100° C. in nitrogen flow transforms most of the product into BNNTs. A high-temperature high-pressure method is also suitable for BNNT synthesis. One method of preparing BNNTs is described in Amanda L. Tiano et al. "Boron Nitride Nanotube: Synthesis and Applications", Proc. SPIE, Vol. 9060, 2014. BNNT are also commercially available, for example, from BNNT, LLC (Newport News, Va. 23606.)

In one embodiment of the present invention, BNNTs are incorporated into a fabric, for example a knitted or woven textile material. Such a fabric may form part of implantable medical devices such as, but not limited to, endovascular grafts, vascular grafts, stent grafts, balloon catheters, meshes, filters (e.g., vena cava filters), tissue scaffolds, myocardial plugs, valves (e.g., venous valves), pelvic implants, various types of dressings, or other known implantable devices. The medical device may be a bifurcated integrated stent-graft, an integrated stent-graft configured for any blood vessel including coronary arteries and peripheral arteries (e.g., renal, superficial femoral, carotid, and the like), a urethral integrated stent-graft, a biliary integrated stent-graft, a tracheal integrated stent-graft, a gastrointestinal integrated stent-graft, or an esophageal integrated stent-graft, for example.

Typically, in stent-graft devices, the fabric material is attached to the stent portion of the devices by, for example, sutures or an adhesive, so that when the stent is expanded alter delivery to the treatment site, the fabric material contacts the vessel wall and provides support for any weakness present.

Figure 1:
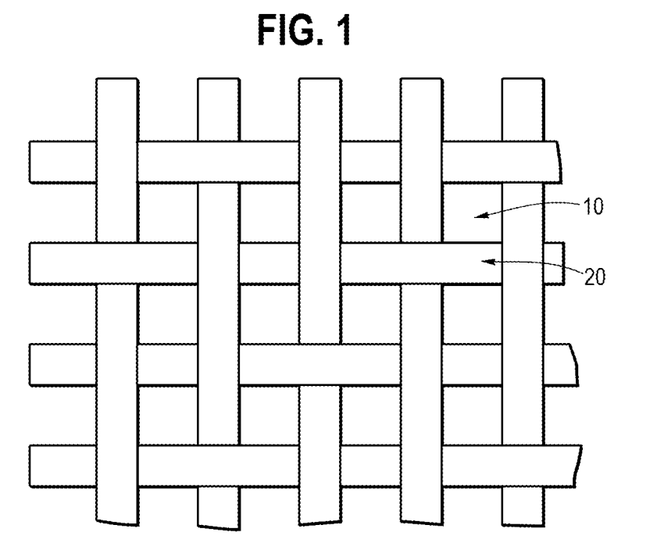
FIG. 1 is an illustration showing a woven fabric material according to one embodiment of the present invention.

Turning now to FIG. 1, there is here illustrated one embodiment of a fabric containing BNNTs. The fabric shown is a woven fabric. However, the present invention also encompasses knitted fabrics including BNNTs incorporated into the fabric as disclosed herein.

Figure 2:
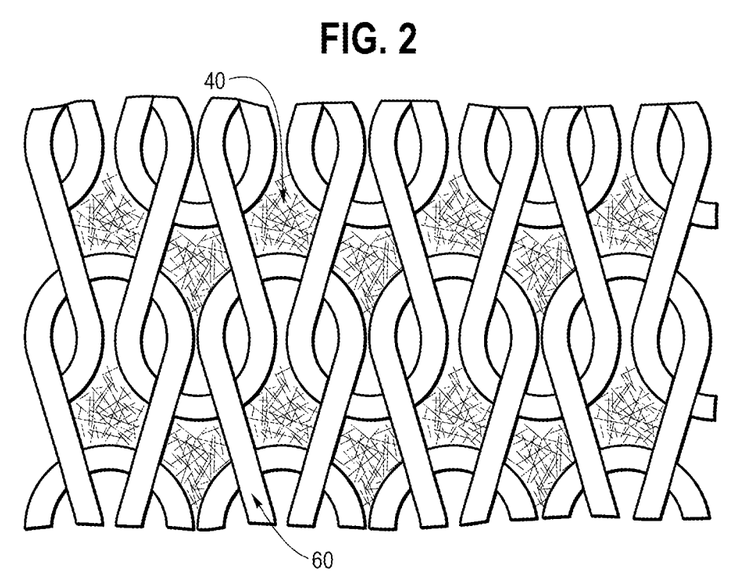
FIG. 2 is an illustration showing a knitted fabric material according to another embodiment of the present invention.

In FIG. 1, strands 20 form a woven fabric material. BNNTs 20 are deposited to form a matrix between the strands 20. In some embodiments, the BNNTs may be contained within a polymer matrix. For example, the matrix may include an elastic polymer, such as polyurethane or an non-fluorinated polymer. The strands may be formed from, for example, at least one of the natural or synthetic textile materials disclosed herein. FIG. 2 illustrates another embodiment of a fabric containing BNNTs. Here, strands 60 form a knitted material. BNNTs 40 are deposited to form a matrix between the strands of the knitted material.

Preferably, the textile material is biocompatible. For example, biocompatible materials from which textile strands may be formed include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be suitable for use as textile strands if they can be rendered biocompatible. For example, surface modification techniques may be employed to impart biocompatibility to such materials. Examples of surface modification techniques include graft polymerization of biocompatible polymers from the material surface, coating of the surface with a crosslinked biocompatible polymer, chemical modification with biocompatible functional groups, and immobilization of a compatibilizing agent such as heparin or other substances.

Natural textile materials include wool, cotton and silk. Synthetic polymers that can be formed into fibers for making textile strands are preferred. For example, suitable polymers include polyethylene, polypropylene, polyaramids, polyacrylonitrile, nylons and cellulose, in addition to polyesters, fluorinated polymers, and polyurethanes as listed above. Desirably, the textile strands comprise biocompatible polyesters. For example, the textile strands may comprise polyethylene terephthalate and PTFE. A preferred commercial example of polyethylene terephthalate especially suited for weaving is DACRON®. These materials have good physical characteristics and are generally inexpensive, easy to handle, and suitable for clinical application.

In various embodiments, the strands include a material such as a polyester, polyethylene terephthalate, a fluorinated polymer, polytetrafluoroethylene (PTFE), expanded PTFE, a polyurethane, polyethylene, polypropylene, polyaramid, polyacrylonitrile, nylon or cellulose or a combination of at least two of these materials. In a preferred embodiment, the strands include polyethylene terephthalate.

The woven or knitted fabric may also include at least one metallic wire interspaced with the textile and BNNT strands. The metallic wire may provide structural support to the graft, thereby eliminating the need for a stent structure, or it may have another function, such as imparting superelastic characteristics or radiopacity to the graft fabric. The metallic wire is preferably formed of a biocompatible metal or alloy. Appropriate metals and alloys may include, for example, stainless steel, nickel-titanium alloy (e.g., NITINOL), gold, platinum, palladium, titanium, tantalum, tungsten, molybdenum, or alloys thereof. Other suitable alloys may include cobalt-chromium alloys such as L-605, MP35N, and Elgiloy; nickel-chromium alloys, such as alloy 625; and niobium alloys, such as Nb-1% Zr, and others.

In certain embodiments, the metal or alloy of the metallic wire may have shape memory/superelastic characteristics that enable the wire to "remember" and recover a previous shape. In the case of nickel-titanium shape memory alloys, the source of the shape recovery is a phase transformation between a lower temperature phase (martensite) and a higher temperature phase (austenite), which may be driven by a change in temperature (shape memory effect) or by the removal of an applied stress (superelastic effect). Strain introduced into the alloy in the martensitic phase to achieve a shape change may be substantially recovered upon completion of a reverse phase transformation to austenite, allowing the alloy to return to the previous shape. Recoverable strains of up to about 8-10° A are generally achievable with nickel-titanium shape memory alloys. Other suitable shape memory alloys for the metallic wire may include, for example, Cu—Zn—Al alloys and Fe—Ni—Al alloys.

Such woven or knitted structures may form a covering for an implantable graft device. Tubular 3-dimensional structures may for part of devices such as tubular stent grafts, vascular grafts and bypass devices. Flat sheet structures may for devices such as hernia patches, skin graft patches, bone stabilization devices or bandages.

Figure 3:
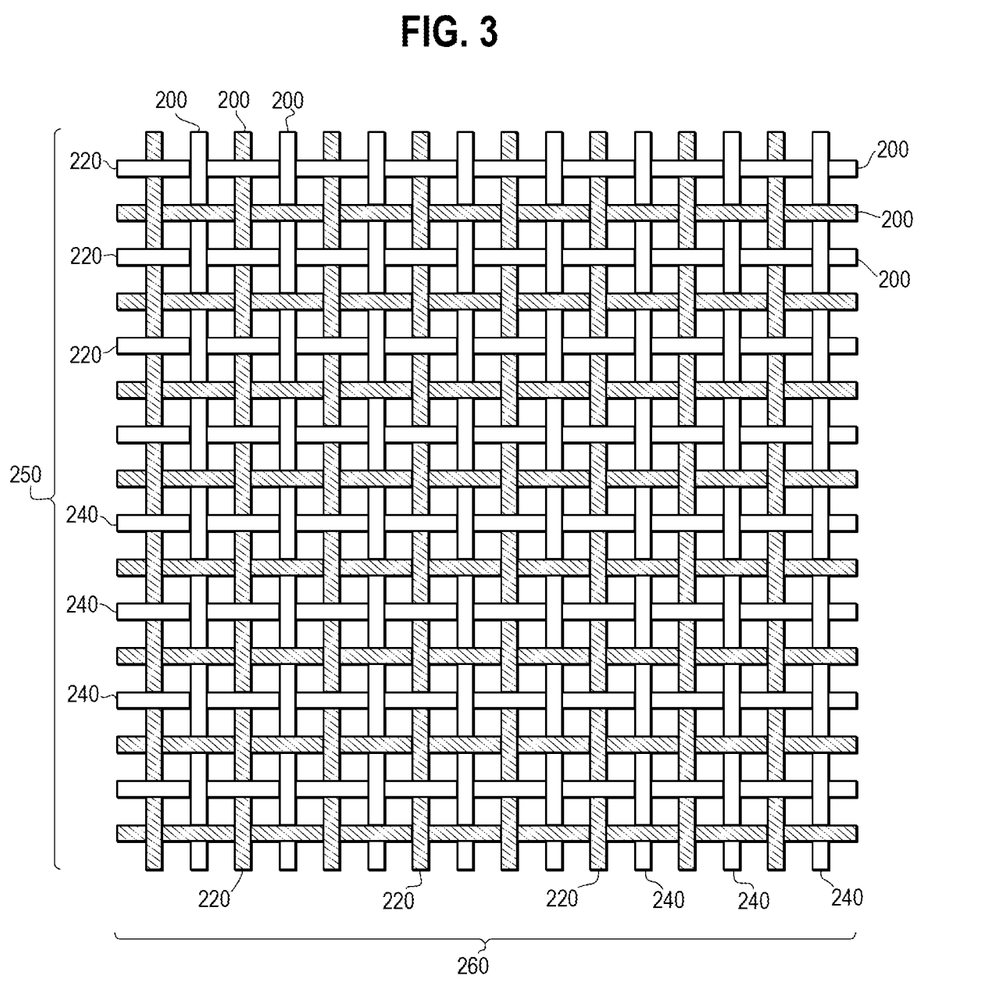
FIG. 3 is an illustration showing another woven fabric material according to one embodiment of the present invention.

In other embodiments, instead of being present between the strands forming the graft, the BNNTs are incorporated into at least some of the strands of a woven or knitted material. FIG. 3 illustrates a woven material including a first plurality 250 of the strands 200 aligned in a warp direction of the woven material, and a second plurality 260 of the strands 200 aligned in a weft direction of the woven material. The warp and weft strands are shown forming a plain weave. However, other weave forms, including those disclosed herein, are also encompassed by the invention.

In one embodiment, each strand of the material is at least partly formed from BNNTs. For example, an individual strand may be formed from BNNTs without the presence of another material. In other embodiments, each individual strand is formed from a combination of BNNTs and another natural or synthetic material, such as those disclosure herein.

Each strand may be formed of a single filament, or may include at least two, three, four, five, six or more filaments aligned with or without a twist. For example, a strand may be formed of one or more BNNT filaments combined with one or more filaments formed from another material. In other embodiments, at least one of the filaments forming the strand may include BNNTs and another textile material.

In one embodiment, the BNNTs are continuously integrated along the filaments of the textile material. In yet another embodiment, the BNNTs are discontinuously integrated along the filaments. In another embodiment, the BNNTs are wrapped around a least a portion of an outside surface of the number of twisted or untwisted filaments. In yet another embodiment, the BNNTs are wrapped around an entire length of an outside surface of the strand.

Returning now to FIG. 3, stands 220 including BNNTs (shaded) may be interwoven with strands 240 not including BNNTs. Here, a first plurality 250 of the BNNT containing strands 220 are aligned in a warp direction of the woven fabric, and a second plurality 260 of the BNNT strands 220 are aligned in a weft direction of the woven fabric. The BNNT strands 220 are interwoven with textile strands 240, which are aligned in both the warp and weft directions of the woven fabric.

In this embodiment, the BNNT containing strands and textile strands not including BNNTs alternate in both the warp and weft directions. In other embodiments of the fabric, the BNNT containing strands may be present in only one of the warp and welt directions.

In one embodiment, all or a majority of the strands forming the knitted of woven fabric are formed from strands including BNNTS. For example, more that 95%, 90%, 80%, 70% or 60% of the strands may include BNNTs. In other embodiments, the woven of knitted fabric is composed primarily of textile strands formed from materials other than BNNTs. For example less than 50%, 40% 30% 10% or 5% of the strands forming the fabric of the device may include BNNT. The other strands in the fabric may be formed of another of the textile materials disclosed herein. For woven devices, the same proportion of BNNT containing strands may be woven in each direction, or each direction may include a different proportion of the BNNT strands. Alternatively, in one direction of the woven fabric there may be one textile strand for every BNNT strand, but in the other direction there may be two (or three, or more) textile strands for every BNNT strand, such that 40% (or 33%, or less) of the strands of the woven fabric are BNNTS. Other combinations of warp and weft direction proportions are also encompassed by the present embodiments.

Figure 4:
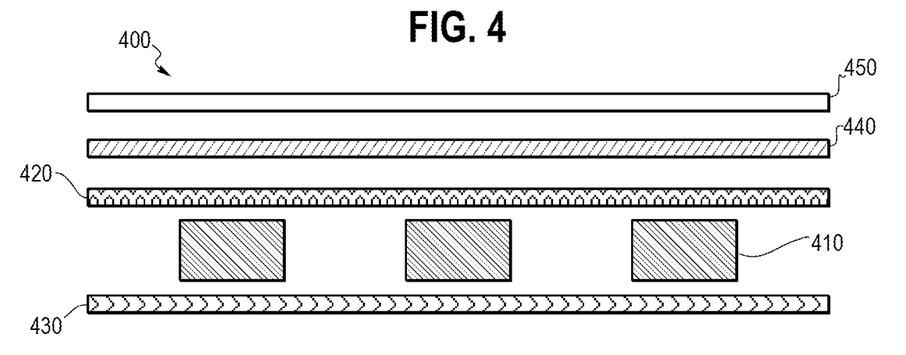
FIG. 4 is an illustration showing a stent device having a graft covering including a layer containing boron nitride nanoparticles.

FIG. 4 illustrates another embodiment of the present invention. Here, medical device 400, for example, a stent device, includes arms 410. Graft material layer 420 forms a covering on the stent and is formed from fabric material that does not include BNNTs. For example, layer 420 may be formed of the natural or synthetic material disclosed herein. In some embodiments, an additional layer 430 of graft material is present such that the arms of the device are sandwiched between two layers of graft material. Layer 440 is posited on layer 420 and includes BNNTs. In some embodiments, layer 440 is formed entirely of BNNTs. In other embodiments, layer 440 includes BNNTs and a carrier material, such as a polymer material.

The polymer carrier material may be, for example, a polyurethane; silicone; polyester; polyolefin; polyisobutylene; ethylene-alphaolefin copolymer; acrylic polymer or copolymer; vinyl halide polymer or copolymer, such as polyvinyl chloride; polyvinyl ether, such as polyvinyl methyl ether; polyvinylidene halide, such as polyvinylidene fluoride and polyvinylidene chloride; polyacrylonitrile, polyvinyl ketone; polyvinyl aromatic, such as polystyrene; polyvinyl ester, such as polyvinyl acetate; copolymer of vinyl monomers with each other and olefins, such as ethylene-methyl methacrylate copolymers, acrylonitrile-styrene copolymers, ABS resins, and ethylene-vinyl acetate copolymers; polyamide, such as Nylon 66 and polycaprolactam; alkyd resin, polycarbonates; polyoxymethylene; polyimide; polyether; epoxy resin, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

In some embodiments, BNNT layer 440 is covered by an additional layer 450. Layer 440, may or may not include BNNTs and will typically form the outermost layer of the device. However, in certain embodiments, multiple layers including BNNTs may be present. The layers containing BNNT may be, but need not be, separated by layers not including BNNTs.

Figure 5:
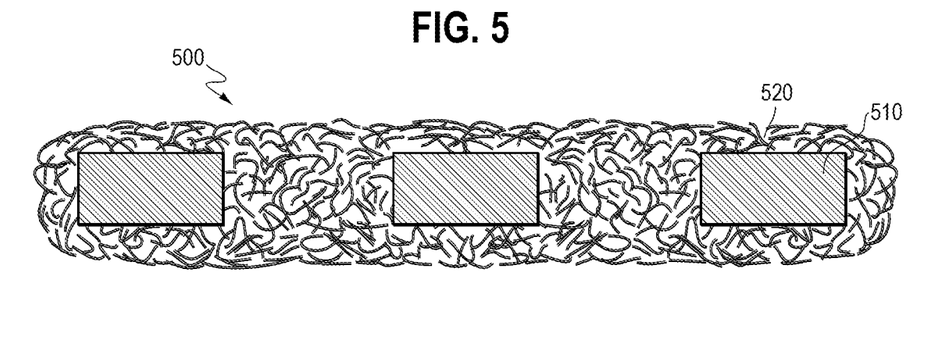
FIG. 5 is an illustration showing a stent having a graft covering formed using an electro-spinning process.

FIG. 5 illustrates another embodiment of the present invention. Here the base structure of a medical device 500, such as a stent arms 510, is embedded in electrospun material 520. Electrospun material 520 may include only BNNTs or may a combination of BNNTs and one of the polymeric fabric material disclosed herein.

For example, the ratio of the combination of BNNTs and the polymeric fabric material may be chosen in such a way to create specific composite material properties. For example, a high amount of the polymeric fabric component may decrease the permeability, elasticity and a high amount of the BNNTs may increase mechanical strength. Ratios could be described in reference to a 1:1 ratio by area of BNNT coverage. The ratio of 1:1 would indicate that half of the area of electrospun material is in some way connected with BNNTs while the other half is not. A change in this ratio would indicate more or less area is covered with BNNTs. In doing so, any sort of pattern of BNNT deposition can be made in order to achieve a desired effect.

Another way to describe BNNT addition to an electrospun material could include BNNT density by weight of the electrospun material. More BNNTs would increase BNNT density in the material and thus increase mechanical and other properties. Less BNNT density would have less effects of BNNT presence. This density descriptive approach applies to materials where BNNTs are uniformly applied to the filaments.

BNNTs may also be incorporated into knitted materials by either functionalizing fabric with BNNTs in all or selected regions of the knitted strand. Common knitting methods may include weft knitting and warp knitting. The specific chosen knitting pattern may increase the elasticity of the fabric which helps to create a specific 3-dimensional shape. Knitted materials may consist of various arrangements of loops that provide more compliance in a fabric. By functionalizing certain loops or fibers in a knitted fabric with BNNTs, it is possible to add stiffness to various axes in various amounts with BNNT materials.

Figure 6A:
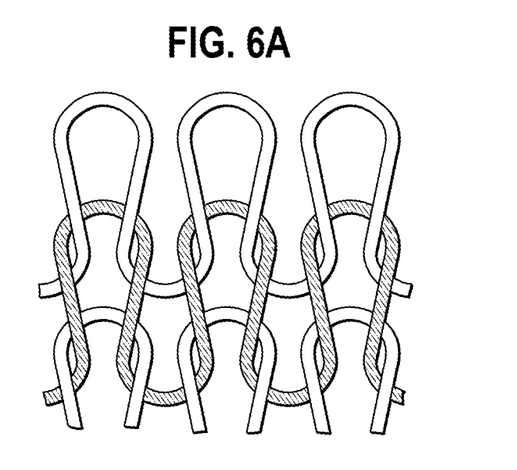
Figure 6B:
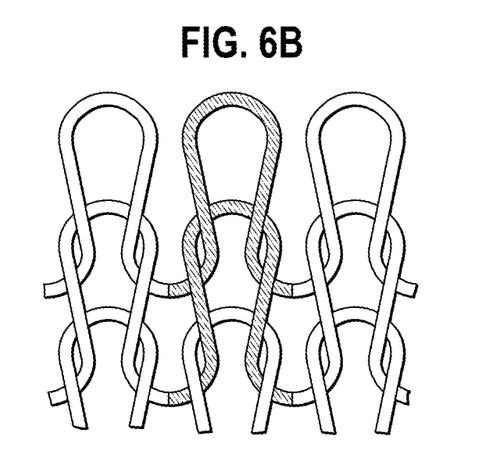

FIG. 6(A-B) illustrates examples of functionalizing a thread within a knitted textile arrangement. In FIG. 6(A), a single thread (dark thread) is functionalized so that BNNTs only adhere to this thread. The adjoining threads (light color) in comparison are not functionalized. Alternatively, or as well as, vertical row of "loops" can be functionalized. FIG. 6(B) shows such an arrangement. Here the dark regions of the knitted strand are functionalized while the lighter colored regions are not.

Various knitted patterns can be formed with, for example, alternating BNNT connected threads and non-BNNT connected threads. Knitted textiles can also be readily be created into 3D shapes with patterns of elevated segments that can be targeted with BNNTs to create stronger textured surface designs.

The BNNT containing devices disclosed herein may also include a therapeutically effective amount of a bioactive agent. For example, the bioactive agent may be incorporated into the BNNT-containing material and/or into another component of the device. For example, in the case of stent-graft devices, the bioactive agent may be incorporated into the strands of the woven or knitted graft material. The bioactive material may be incorporated during the manufacturing process, for example before the weaving or knitting process. In other embodiments, the bioactive agent may be impregnated into the fabric after the strands are formed. In other embodiments, the bioactive material is present in a coating on the graft portion of the device.

The bioactive agent may be selected to perform a desired function upon implantation. Bioactive agents within the scope of the present embodiments include antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such drugs include doxorubicin, camptothecin, etoposide, mitoxantrone, cyclosporine, epothilones, napthoquinones, 5 fluorouracil, methotrexate, colchicines, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone) mitomycin and derivatives or analogues of these agents.

Preferred bioactive agents include restenosis-inhibiting agents a, including but not limited to microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor).

Certain bioactive agents may be present in more than one polymorphic form. For example, paclitaxel may be present as at one of Solid forms of amorphous paclitaxel ("aPTX"), dihydrate crystalline paclitaxel ("dPTX") and anhydrous crystalline paclitaxel.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A medical device for introduction by a delivery system, the medical device comprising a fabric comprising a knitted or woven textile material and a plurality of boron nitride nanotubes, wherein the boron nitride nanotubes are present in a matrix between strands of the knitted or woven textile material or in the strands of the knitted or woven textile material.

2. The medical device of claim 1, wherein the knitted or woven textile material is a woven textile material.

3. The medical device of claim 1, wherein the knitted or woven textile material is a knitted textile material.

4. The medical device of claim 1, wherein the textile material comprises a material selected from the group consisting of a polyester, polyethylene terephthalate, a fluorinated polymer, polytetrafluoroethylene (PTFE), expanded PTFE, a polyurethane, polyethylene, polypropylene, polyaram id, polyacrylonitrile, nylon and cellulose.

5. The medical device of claim 4, wherein the textile material comprises polyethylene terephthalate.

6. The medical device of claim 1, wherein the boron nitride nanotubes are present in the strands of the knitted or woven textile material.

7. The medical device of claim 6, wherein the strands comprise a plurality of filaments of the textile material, wherein the filaments are twisted and wherein the boron nitride nanotubes are continuously integrated along the filaments.

8. The medical device of claim 6, wherein the strands comprise a plurality of filaments of the textile material, wherein the filaments are twisted and wherein the boron nitride nanotubes are discontinuously integrated along the filaments.

9. The medical device of claim 6, wherein the strands comprise a plurality of twisted filaments of the textile material and the boron nitride nanotubes are wrapped around a least a portion of an outside surface of the plurality of twisted filaments.

10. The medical device of claim 9, wherein the boron nitride nanotubes are wrapped around an entire length of an outside surface of the strand.

11. The medical device of claim 6, wherein the strands comprise a plurality of filaments of the textile material, wherein the filaments are not twisted and wherein the boron nitride nanotubes are continuously integrated along the filaments.

12. The medical device of claim 1, wherein the knitted or woven textile material is a woven textile material and wherein the boron nitride nanotubes are present in a matrix between strands of the woven textile material.

13. The medical device of claim 1, wherein the knitted or woven textile material is a knitted textile material and wherein the boron nitride nanotubes are present in a matrix between strands of the knitted textile material.

14. A medical device for introduction by a delivery system, the medical device comprising:
   a stent having a luminal surface and an abluminal surface, and
   a graft attaching to the abluminal surface, wherein the graft comprises a knitted or woven textile material and a plurality of boron nitride nanotubes, wherein the boron nitride nanotubes are present in a matrix between strands of the knitted or woven textile material or in the strands of the knitted or woven textile material.

15. The medical device of claim 14, wherein the stent comprises a material selected from the group consisting of a metal, a metal alloy and a polymeric material.

16. The medical device of claim 14, wherein the textile material comprises a material selected from the group consisting of a polyester, polyethylene terephthalate, a fluorinated polymer, polytetrafluoroethylene (PTFE), expanded PTFE, a polyurethane, polyethylene, polypropylene, polyaramid, polyacrylonitrile, nylon and cellulose.

17. The medical of claim 16, wherein the textile material comprises expanded PTFE.

18. The medical device of claim 14, wherein the medical device is a stent-graft.

19. The medical device of claim 1, wherein the medical device is a stent-graft.

* * * * *